United States Patent [19]
Uchiyama et al.

[11] Patent Number: 4,955,366
[45] Date of Patent: Sep. 11, 1990

[54] ULTRASONIC THERAPEUTICAL APPARATUS

[75] Inventors: Naoki Uchiyama; Syuichi Takayama, both of Hachioji; Masakazu Gotanda, Sagamihara; Tetsumaru Kubota, Hachioji; Takashi Tsukaya, Hachioji; Kouichiro Ishihara, Hachioji; Kuniaki Kami, Hachioji; Naomi Sekino, Hachioji; Akira Murata, Hachioji; Masaki Hayashi, Hachioji, all of Japan

[73] Assignee: Olympus Optical Co., Ltd., Japan

[21] Appl. No.: 271,662

[22] Filed: Nov. 15, 1988

[30] Foreign Application Priority Data

Nov. 27, 1987 [JP] Japan .................. 62-298989
Jun. 15, 1988 [JP] Japan .................. 63-149037
Jun. 15, 1988 [JP] Japan .................. 63-149038

[51] Int. Cl.$^5$ .................. G01N 29/00; A61B 8/00
[52] U.S. Cl. .................. 128/24 A; 128/660.030
[58] Field of Search .................. 128/660.03, 24 A, 328; 606/127, 128

[56] References Cited

U.S. PATENT DOCUMENTS

| | | | |
|---|---|---|---|
| 4,586,512 | 5/1982 | Dohuu et al. | 128/660.03 |
| 4,757,820 | 7/1988 | Itoh | 128/24 A X |
| 4,807,627 | 2/1989 | Eisenmenger | 128/328 S |
| 4,823,773 | 4/1989 | Naser et al. | 128/328 S X |
| 4,836,191 | 6/1989 | Noske et al. | 128/328 S X |

FOREIGN PATENT DOCUMENTS

63-51853 3/1988 Japan .................. 128/328

Primary Examiner—Francis Jaworski
Attorney, Agent, or Firm—Ostrolenk, Faber, Gerb & Soffen

[57] ABSTRACT

A ultrasonic therapeutical apparatus comprises a plurality of ultrasonic vibrators which are disposed in a plurality of concentric circular rows and defining a ultrasonic shock wave generator. The apparatus also includes control means for independently controlling the frequency and the phase with which the ultrasonic vibrators in the respective raws are driven as well as the output levels thereof, thereby allowing only a positive pressure of the resultant ultrasonic wave to be increased while suppressing a negative pressure thereof to eliminate a cavitation effect.

25 Claims, 11 Drawing Sheets

ULTRASONIC THERAPEUTICAL APPARATUS

FIELD OF THE INVENTION AND RELATED ART STATEMENT

The invention relates to a ultrasonic therapeutical apparatus, and more particularly, to a ultrasonic therapeutical apparatus which focusses ultrasonic shock wave generated by ultrasonic vibrators to a target region to be treated within a physical body from a location outside the body for purpose of therapy.

As disclosed in Japanese Laid-Open Patent Application No. 145,131/1985 or the like, a calculus fracture apparatus is known as one of ultrasonic therapeutical apparatus which produces shock wave externally of a physical body and which focusses the shock wave upon a calculus located within the body to fracture it. The present applicant has previously proposed ultrasonic therapeutical apparatus of the kind described as disclosed in Japanese Patent Application No. 94,973/1987 and Japanese Patent Application No. 67,519/1987.

A calculus fracture apparatus of the kind described generally comprises a ultrasonic shock wave generator including a plurality of ultrasonic vibrators, which may be formed by piezoelectric elements, which are disposed in an array in a mosaic pattern on a spherical surface which is defined by a mounting plate. The shock wave generator is disposed in contact with the surface of a physical body with a water bag in which ultrasonic wave transmitting fluid such as water is filled interposed therebetween, thus directing and focussing ultrasonic shock wave upon a calculus or calculi which are formed within kidney, bladder, gall, biliary ducts or the like for purpose of fracture. The ultrasonic shock wave is generated in response to the application of a pulse voltage to the ultrasonic vibrators while the location of a calculus is recognized by means of a ultrasonic observation unit.

Another form of ultrasonic therapeutical apparatus comprises a ultrasonic heating apparatus which is commonly referred to as hyperthermia. This apparatus focuses a ultrasonic wave upon a tumor or the like which is formed within a physical body in order to achieve a heating remedy by irradiation. This apparatus is constructed in entirely the same manner as the calculus fracturing apparatus. Accordingly, a ultrasonic therapeutical apparatus to be described below includes such ultrasonic heating apparatus as well as a calculus fracturing apparatus.

In the ultrasonic therapeutical apparatus, the focussing of a ultrasonic wave for purpose of therapy results in producing a negative pressure as well as a positive pressure at the focal point of the wave, where a cavitation occurs. If a greater ultrasonic wave output is focussed upon such point for purpose of therapy, the magnitude of the negative pressure increases as the positive pressure increases in magnitude, resulting in the likelihood that a normal tissue of a physical body may be destroyed by cavitation.

A conventional ultrasonic therapeutical apparatus entirely lacks means which examines the presence of an abnormality of such apparatus or which examines if the apparatus is actually operating in a normal manner. More specifically, there has been no ultrasonic therapeutical apparatus which is provided with recognition means capable of directly determining whether the ultrasonic shock wave is actually concentrated upon an intended location or whether the sound pressure of the ultrasonic wave or its wave form as measured at a focal point is achieved in an intended manner. Accordingly, if there occurs some abnormality in the therapeutical apparatus, for example, if the focal point of the ultrasonic wave is displaced for some reason, if the sound pressure at a focal point is excessively high, or if the ultrasonic wave exhibits a sound pressure waveform other than intended, the therapy conducted may result in a failure to fracture a calculus or may cause a serious damage to the tissue of a physical body by concentrating a ultrasonic wave at a location other than the location of a calculus or tumor or by providing a greater output than intended for the therapy.

It will be appreciated that the operational performance of individual piezoelectric elements, which form the ultrasonic vibrators, are essential, together with the increased number thereof, to produce a ultrasonic wave of a high intensity which is required to achieve an improved efficiency of therapy. However, in the conventional practice, there has been no provision which examines the operational efficiency of individual piezoelectric elements as well any change in their responses, even though the need for such provision has been recognized.

OBJECT AND SUMMARY OF THE INVENTION

It is a principal object of the invention to overcome the described difficulties found in conventional ultrasonic therapeutical apparatus as mentioned above, by providing a ultrasonic therapeutical apparatus which allows only a positive pressure to be increased while suppressing an increase in a negative pressure, which enables a ultrasonic shock wave of a high intensity to be produced which can be focussed to a higher degree, and which provides an enhanced safety to physical bodies, and a high conversion efficiency and allows an efficient and proper therapy.

It is another object of the invention to provide a ultrasonic therapeutical apparatus which is capable of examining the location of a focal point where a ultrasonic wave is to be focussed, a sound pressure waveform at such focal point and the presence of any abnormality in the apparatus before the therapy is initiated, all in a simple manner.

It is a further object of the invention to provide a ultrasonic therapeutical apparatus which allows any change in the response of individual ultrasonic vibrators comprising piezoelectric elements to be examined in a facilitated manner by utilizing simple means, and which allows an optimum therapeutical effect to be assured by enabling a remedy against such change.

In accordance with the invention, a ultrasonic shock wave generator which is used to generate a ultrasonic wave comprises a plurality of rows of ultrasonic vibrators, and is associated with control means which controls the frequency, the phase and/or output levels of the respective rows independently. In this manner, the magnitude of a negative pressure produced can be suppressed while allowing the output to be increased to achieve a higher therapeutical efficiency. By allowing only a positive pressure to be increased, a likelihood that normal tissues within a physical body may be destroyed by cavitation which may occur at the focal point is avoided, thus assuring the safety to physical bodies while providing an increased conversion efficiency to allow an efficient therapy by a ultrasonic therapeutical apparatus.

The ultrasonic vibrators, formed by piezoelectric elements, are disposed on a spherical surface in a mosaic pattern to define a ultrasonic shock wave generator, and a movable ultrasonic sensor is disposed at the focal point thereof so that before the therapy is conducted, the sensor allows the location of the focal point, sound pressure and waveform of the ultrasonic to be recognized in order to detect any abnormality of the therapeutical apparatus. In this manner, there is provided a ultrasonic therapeutical apparatus which enables a therapy with an added safety to a patient while preventing any serious accident which may be caused by any trouble thereof.

Individual ultrasonic waves which are delivered by the plurality of ultrasonic vibrators are focussed at a single point by the ultrasonic wave generator, and in accordance with the invention, reflection means is provided which causes the individual ultrasonic waves to be returned to the respective piezoelectric elements from which such waves are emitted. This allows any change in the response of individual piezoelectric elements to be detected in a simple manner, enabling any required action against degraded or faulty vibrators to be taken immediately. In this manner, the ultrasonic therapeutical apparatus of the invention is capable of maintaining an optimum therapeutical effect.

DETAILED DESCRIPTION OF PREFERRED EMBODIMENTS

Figure 19:
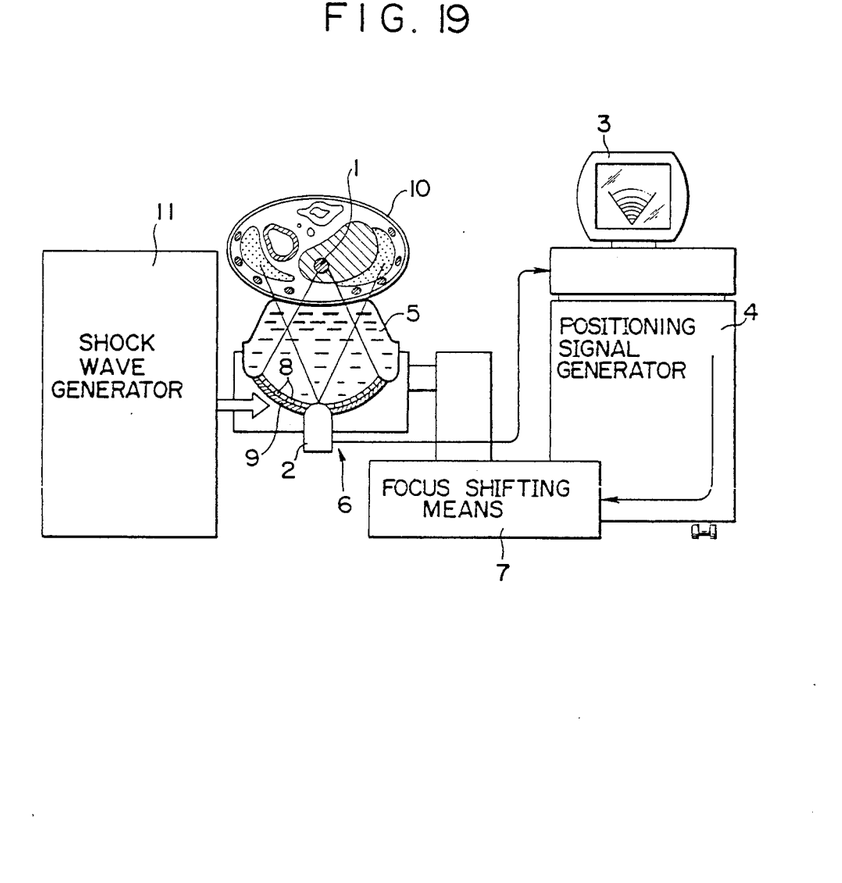
FIG. 19 is a schematic view and block diagram of an entire ultrasonic therapeutical apparatus.

Before describing embodiments of the invention in detail, an entire arrangement of a ultrasonic therapeutical apparatus in accordance with the invention will be initially described with reference to FIG. 19. The apparatus comprises observation means (position detecting means) which detects the location of a calculus or calculi within a physical body, means 4 for generating a positioning signal, focus shifting means 7, and shock wave generating means 11 which is adapted to fracture a calculus 1 or which applies a heating action upon a tumor.

The observation means comprises a ultrasonic observation unit 2 which emits a ultrasonic wave toward a physical body 10 of a human being in order to detect the location of a calculus 1 or tumor located therein, and a display unit 3 which receives a detection signal from the observation unit to display the location of a calculus or the like on a screen as may be formed by CRT.

Means 4 for producing a positioning signal presets an instruction marker at a point on the screen of the display unit 3, and delivers a control signal to the focus shifting means 7 so that the focal point of the shock wave which is used for the purpose of therapy be situated at the location of the instruction marker.

Thus, means 4 utilizes an arrangement for displaying an image of a calculus, the location of which is detected, and applies an optimum signal to the screen of the display unit 3 as by a write pen. The optimum signal is formed of (1) a signal indicating the sequence in which calculi are fractured as in the sequence of the decreasing size thereof or a signal indicating the sequence of areas of a coral calculus which are to be sequentially fractured when an operator such as a physician has recognized the size or the number of calculus or calculi displayed; or (2) a signal used to change the focal point of the fracturing shock wave which is required as a result of a displacement of the location of the calculus which occurs as it is being fractured and which is derived by periodically detecting the location and the size of the calculus. The signal entered by the write pen is stored as a treating sequence in a memory, and a resulting positioning signal is read therefrom to be supplied to the focus shifting means 7 when the fracturing operation is to be initiated.

The focus shifting means 7 is operable to move a water bag 5 and a ultrasonic shock wave generator 6, to be described later, in accordance with the positioning signal as by utilizing a numerically controlled robot in order to focus a shock wave to be used for the therapy upon a calculus or tumor. The generator 6 comprises ultrasonic vibrators 8, as may be formed by piezoelectric elements, which are secured on the front surface of a mounting plate 9 in a mosaic pattern so that a shock wave generating surface defined at their front surface is directed toward the physical body 10. The water bag 5 formed of a soft resin material or the like and including means for injecting a fluid and means for controlling the pressure thereof is interposed between the generator 6 and the physical body 10. Usually, a shock wave transmitting liquid such as water fills the bag 5. The ultrasonic vibrators 8 are driven by a ultrasonic pulse voltage generator circuit 11.

Figure 1:
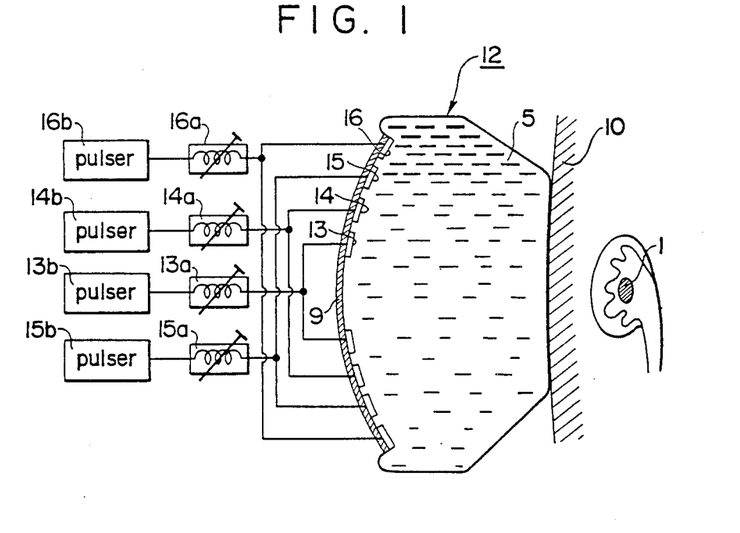
FIG. 1 is a schematic illustration of a ultrasonic shock wave generator of a ultrasonic therapeutical apparatus according to a first embodiment of the invention.
Figure 2:
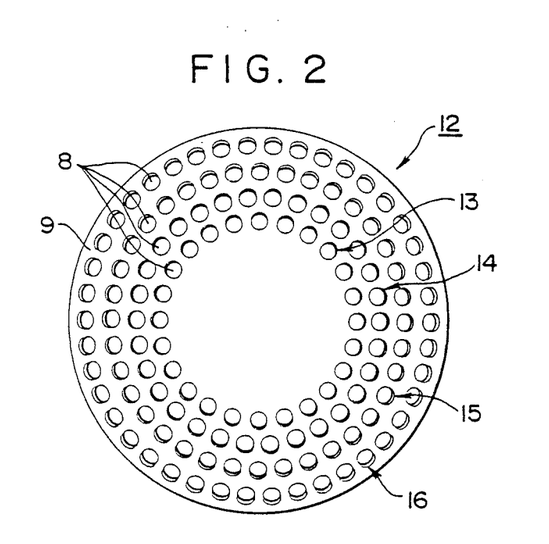
FIG. 2 is a front view of the shock wave generator shown in FIG. 1.

FIGS. 1 and 2 are a schematic view, partly in section, and a front view of a shock wave generator of a ultrasonic therapeutical apparatus according to a first embodiment of the invention. Specifically, the apparatus includes a shock wave generator 12 which includes a mounting plate 9 in the form of part of a spherical shell. An array of concentric circular rows, which are four in number in an example shown in FIG. 2, of disc-shaped ultrasonic vibrators 8, which may be formed by piezoelectric elements, is disposed on the front surface of the mounting plate 9. Specifically, the innermost row 13 includes 24 ultrasonic vibrators, a second outer row 14 includes 30 ultrasonic vibrators, a third outer row 15 includes 36 ultrasonic vibrators and an outermost row 16 includes 42 ultrasonic vibrators, each disposed in a concentric circular row. The respective rows 13, 14, 15 and 16 of ultrasonic vibrators are connected to pulse generators 13$b$, 14$b$, 15$b$ and 16$b$, respectively, through delay circuits 13$a$, 14$a$, 15$a$ and 16$a$, respectively, as shown in FIG. 1. It is to be understood that in FIG. 1, each row 13 to 16 of ultrasonic vibrators is shown as a linear array in order to simplify the illustration. However, it should be understood that the phase of ultrasonic waves generated by the respective ultrasonic vibrators of each row 13 to 16 can be controlled by the associated delay circuits 13$a$ to 16$a$. In addition, the pulse generators 13$b$ to 16$b$ are operable to control the frequency and the amplitude with which the individual ultrasonic vibrators are driven as well as their output levels for each row. The ultrasonic observation unit 2 shown in FIG. 19 is omitted from illustration in FIG. 1.

In the shock wave generator 12 described above, each row 13 to 16 of ultrasonic vibrators is driven at a frequency which is a selected multiple of the frequency with which the ultrasonic vibrators of its immediately adjacent inner row are driven. In the present example, the multiple is equal to two. Thus, the vibrators in the row 14 which is located immediately outside the row 13 is driven with a frequency which is twice the frequency with which the ultrasonic vibrators in the row 13 are driven. Also, the ultrasonic vibrators in the next outer row 15 are driven with a frequency which is nearly twice the frequency with which the ultrasonic vibrators in the row 14 are driven. Finally, the ultrasonic vibrators in the outermost row 16 are driven with a frequency which is nearly twice the frequency with which the ultrasonic vibrators in the row 15 are driven. Considering a change with time of the sound pressure of ultrasonic waves from the ultrasonic vibrators in the individual rows 13 to 16 which are focussed at a single focal point, the phase of the individual ultrasonic waves are controlled by the delay circuits 13$a$ to 16$a$ so that the locations of the sound pressure maxima of ultrasonic waves produced by the individual rows 13 to 16 coincide with each other at the single point.

Figure 3:
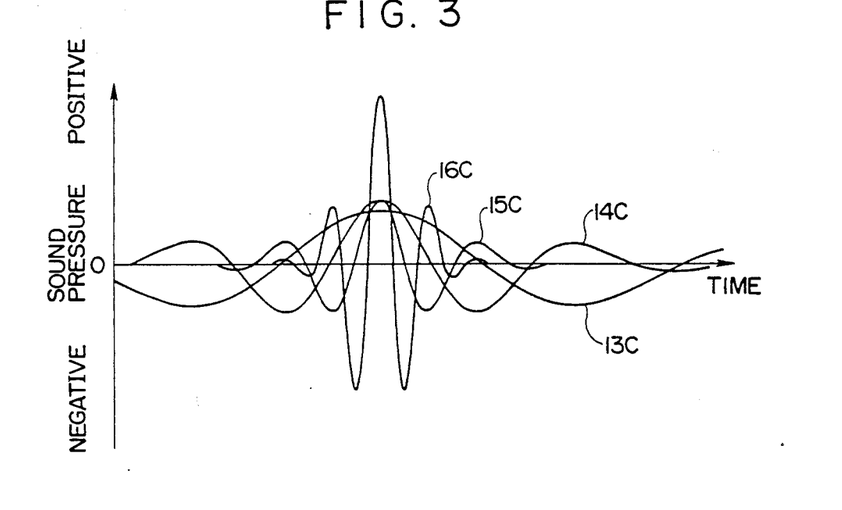
FIG. 3 graphically shows the waveforms of individual ultrasonic wave produced by rows of ultrasonic vibrators contained in the ultrasonic shock wave generator of FIG. 1.
Figure 4:
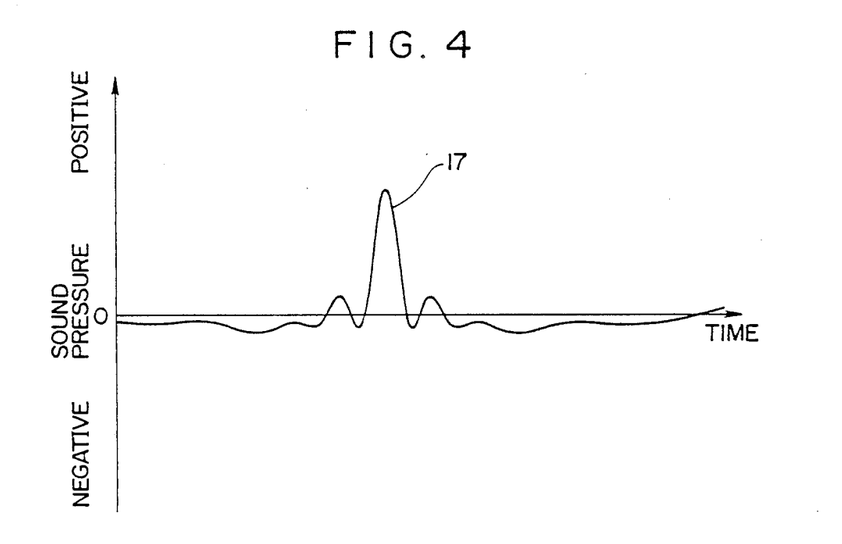
FIG. 4 graphically shows the waveform of a synthesized wave formed by the individual waves shown in FIG. 3.

The sound pressure of the ultrasonic wave generated by the respective rows 13 to 16 of ultrasonic vibrators at a focal point where they are focussed together is graphically shown in FIG. 3, where the ordinate represents the sound pressure and the abscissa represents the time. Specifically, a waveform 13C represents a change of the sound pressure of ultrasonic wave produced by the row 13 with time, and similarly waveforms 14C, 15C and 16C represent a change in the sound pressure of ultrasonic waves produced by the respective rows 14, 15 and 16, respectively, with time. It will be noted that these ultrasonic waves are controlled so that they are in phase at the point of their maximum sound pressure. As a consequence, the sound pressure of the resultant ultrasonic wave at the focal point changes with time in a manner graphically illustrated in FIG. 4. It will be noted that while the individual waveforms 13C to 16C of ultrasonic waves generated by the individual rows 13 to 16 have both positive and negative pressure components which are substantially equal to each other as shown in FIG. 3, the resultant ultrasonic wave 17 at the focal point has its negative pressure suppressed relative to the sound positive pressure, as illustrated in FIG. 4.

Accordingly, an increased output may be allowed to develop at the focal point in order to enhance the therapeutical effect without causing a cavitation mentioned previously, since only the positive pressure is allowed to increase while suppressing the negative pressure, thus avoiding the likelihood of destroying normal tissues of the physical body and enabling an efficient therapy in a safe manner. The negative pressure of the resultant ultrasonic wave may be further reduced by controlling the sound pressures of the ultrasonic waves generated by the individual rows 13 to 16 by utilizing the pulse generators 13$b$ to 16$b$.

It is to be noted that individual ultrasonic vibrators, which are used to define the rows 13 to 16, do not require any special processing, but usual vibrators can be used directly, thus maintaining their high conversion efficiencies.

Figure 5:
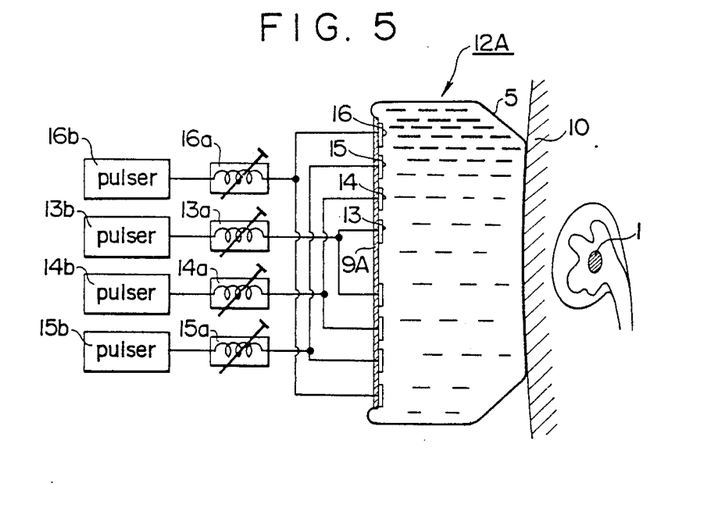
FIG. 5 is a schematic illustration of a ultrasonic shock wave generator of a ultrasonic therapeutical apparatus according to a second embodiment of the invention.

In a second embodiment of the invention shown in FIG. 5, a ultrasonic shock wave generator 12A comprises an array of concentric circular rows 13 to 16 of piezoelectric elements 8 which are mounted on the inner surface of a planar mounting plate 9A, rather than a spherical mounting plate. The focussing of ultrasonic waves developed by the respective rows may be achieved by controlling the phase of the individual vibrators 8 so that the resulting ultrasonic wave may be focussed at a single point, or alternatively, a focussing acoustical lens may be disposed on the front side of the generator 12A. The pulse generators 13$b$ to 16$b$ and the delay circuits 13$a$ to 16$a$ are of the similar construction as mentioned previously, and can be used in a similar manner with a similar effect.

In the described embodiments, the frequency and the phase with which the individual vibrators are driven have been controlled in order to focus the individual ultrasonic waves upon a single point. However, the output levels of the ultrasonic waves may be changed as well. The output level of the ultrasonic wave can be changed by controlling the drive voltage applied to the vibrators, or by changing the number, the variety, the thickness of their damping layer, or configuration of the ultrasonic vibrators.

Figure 6:
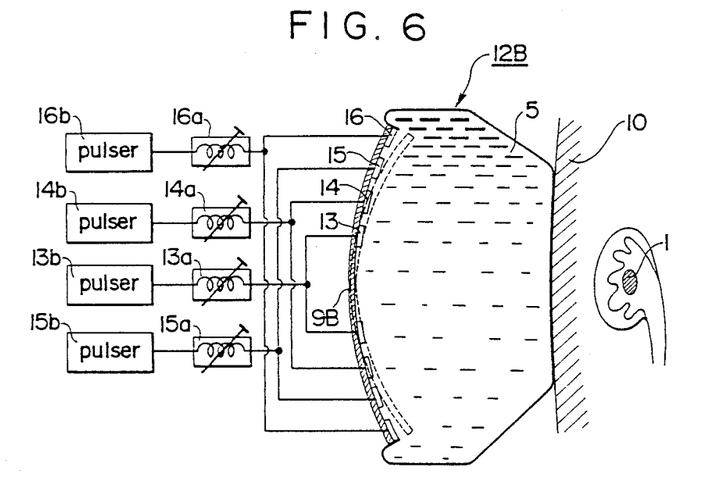
FIG. 6 is a schematic illustration of a modified mounting plate on which the ultrasonic vibrators are mounted.

Instead of using the delay circuits mentioned above, the individual ultrasonic waves may be focussed upon a single point by controlling the distance of the individual ultrasonic vibrators in each row to the focal point. Specifically, FIG. 6 shows a shock wave generator 12B in which ultrasonic vibrators 8 are mounted on a mounting plate 9B which is not on a spherical or planar plane, but it has an increased radius of curvature as compared with the spherical mounting plate shown in dotted lines, so that the ultrasonic waves generated by the respective rows 13 to 16 are focussed at a single point where their maxima of sound pressure are located. It will be seen that the ultrasonic vibrators located remote from the central point on the mounting plate have an increasing distance from a focal point, which provides an equivalent effect to a delaying effect. In this manner, the delay circuits can be dispensed with, or the delay circuits 13a to 16a, if used, may be constructed to exhibit reduced delay times, thus simplifying the circuit arrangement.

Figure 7:
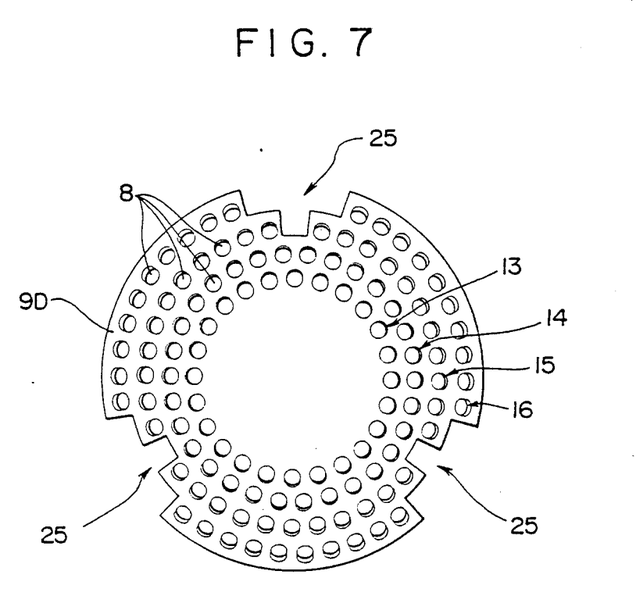
FIGS. 7 to 9 are front views of other modifications of the mounting plate on which the ultrasonic vibrators are mounted.

FIG. 7 shows a modified mounting plate 9D on which ultrasonic vibrators are mounted. Specifically, the mounting plate 9D is formed with notches 25 which are formed at circumferentially spaced apart areas and extending radially inward from the outer peripheral edge. The underlying concept is that a reduced number of ultrasonic vibrators is sufficient to produce a sound pressure of a reduced magnitude because of the improved focussing efficiency even though an outer row may include an increased number of ultrasonic vibrators. If the modified mounting plate 9D is used, the operation and the effect remain substantially unchanged. As a direct effect of reducing the number of ultrasonic vibrators in the outer row or rows, the drive circuit can be simplified and the ultrasonic observation unit may be located within a selected one of the notches 25.

Figure 8:
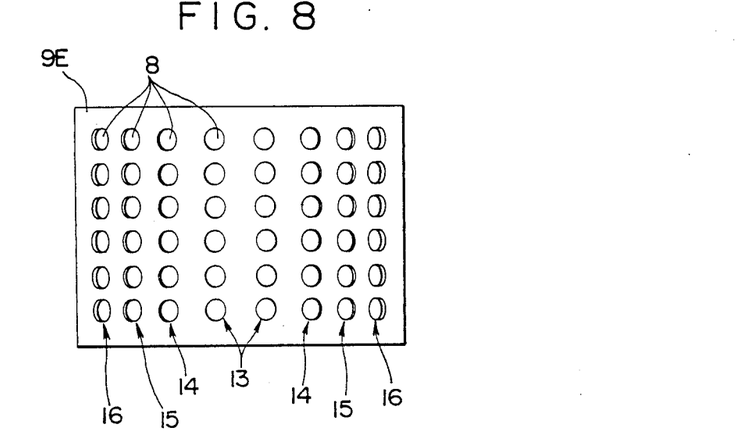
Figure 9:
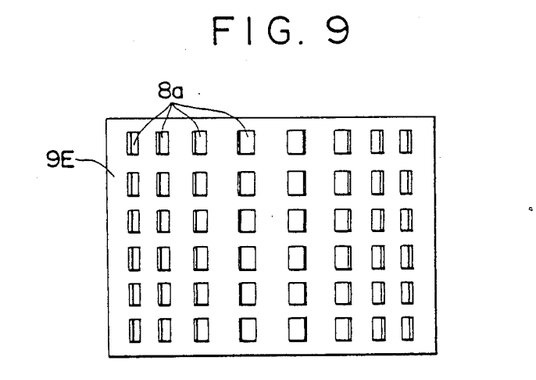

FIGS. 8 and 9 show further alternatives where flat, rectangular plates are flexed to define a concave surface, which represents the plane of a mounting plate 9E. As shown in FIG. 8, a plurality of disc-shaped ultrasonic vibrators 8 may be disposed on the inner surface of the mounting plate 9E so that they are aligned with each other in both vertical and horizontal directions. Alternatively, a plurality of square-shaped ultrasonic vibrators 8a may be disposed on the mounting plate 9E so that they are aligned with each other in both vertical and horizontal directions. The concave configuration of the mounting plate 9E is effective to focus the individual ultrasonic waves from the rows 13 to 16 onto a line segment rather than at a single point, and can be effectively used when treating a calculus of an increased size. Where a tumor located within the physical body is to be heated by the application of the ultrasonic wave, the linear focussing of the ultrasonic wave is effective to achieve a heating effect over an increased area, thus enhancing the therapeutical effect. In other respects, the arrangement and the effect are similar to those described above. Obviously, the mounting plate 9E may define a spherical shell or planar plane.

Figure 10:
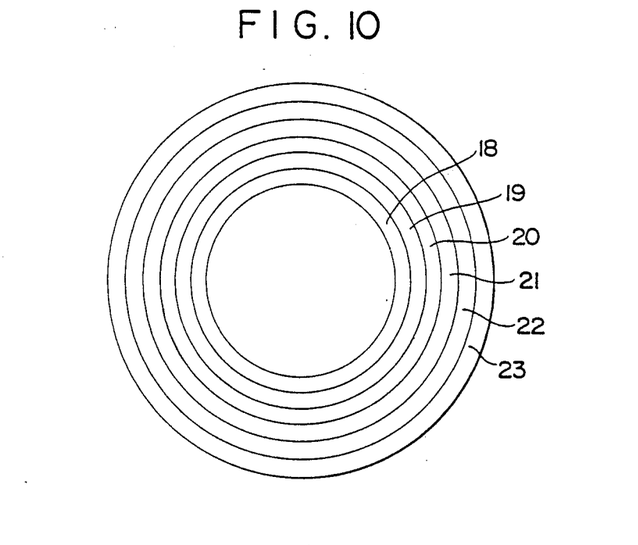
FIGS. 10 and 11 are front views of other forms of ultrasonic vibrators which may be mounted on a mounting plate.
Figure 11:
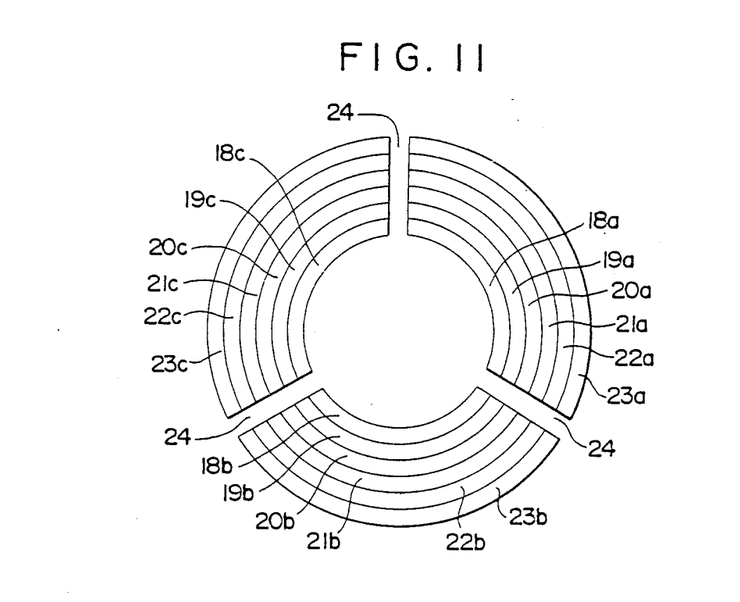

In the shock wave generators 12, 12A and 12B of the described embodiments, the rows 13 to 16 of ultrasonic vibrators 8 have been disposed on concentric circles as shown in FIG. 1, but alternatively, a plurality of ultrasonic vibrators, which are annular in configuration, may be disposed on concentric circles as shown in FIG. 10. In this instance, ultrasonic vibrators 18 to 23 are independently connected to corresponding pulse generators through associated delay cirsuits, both not shown, in a similar manner as described in connection with the described embodiments. The operation remains substantially the same as with the shock wave generator 12, with a similar effect.

As a modification, the annular ultrasonic vibrators 18 to 23 shown in FIG. 10 may be divided into a plurality of vibrators 18a to 23a, 18b to 23b and 18c to 23c, which are shaped to define arcs of circles having different diameters and which are disposed on a plurality of concentric circles. It will be noted that gaps 24 are left between adjacent ultrasonic vibrators, and the ultrasonic observation unit 2 or means such as observation ultrasonic vibrators which are used to detect the location of a calculus 1 may be disposed in such gap. When the ultrasonic vibrators are defined by arcuate vibrators, the operation remains substantially the same as mentioned above, with a similar effect.

As is recognized, a ultrasonic vibrator has a resonant frequency, and can be efficiently driven at a limited drive frequency. However, a damping layer may be applied to such vibrator to broaden the range of drive frequencies. Alternatively, a broad band vibrator as may be formed by PVF (polyvinylidene fluoride) may be used with a drive frequency in a manner mentioned above in connection with the embodiment shown in FIG. 1. The resonant frequency of the individual vibrators may be chosen so that the effect of the invention is achieved.

Figure 12:
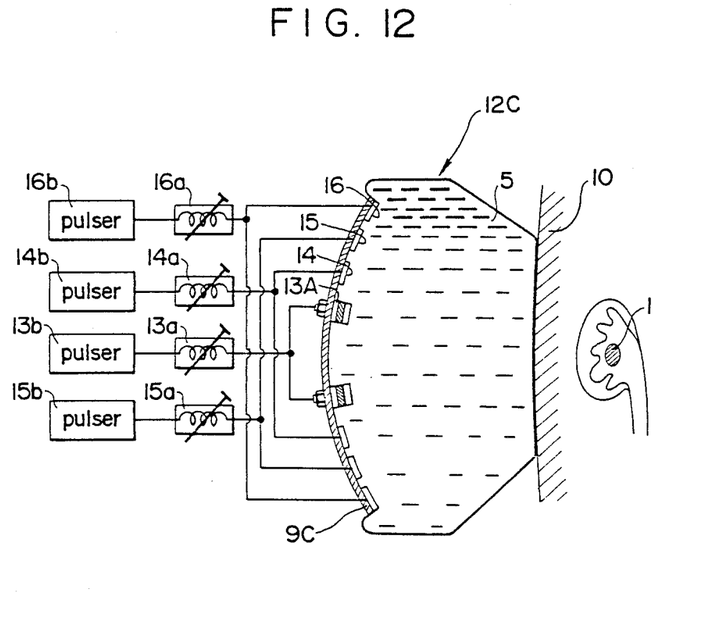
FIG. 12 is a schematic illustration of a further form of ultrasonic vibrator mounted on a mounting plate.

As mentioned previously, the negative pressure of the resultant ultrasonic wave may be further reduced by controlling the sound pressure of the individual ultrasonic waves generated by the respective rows 13 to 16 of vibrators. Because the inner row includes vibrators which are less in number and exhibit a reduced focussing efficiency, it is required that a greater sound pressure be developed. To accommodate for this, a bolted Langevin vibrator may be used for an inner row 13A for the sake of an improved drive efficiency or an increased sound pressure. As is well known, a bolted Langevin vibrator comprises a vibrator held between a pair of metal blocks, which are bolted together. This improves the drive efficiency, allowing associated pulse generator 13b to be simplified. While a bolted Langevin vibrator is used for the innermost row 13A alone in FIG. 12, such vibrator may also be used in other row as required.

Figure 13:
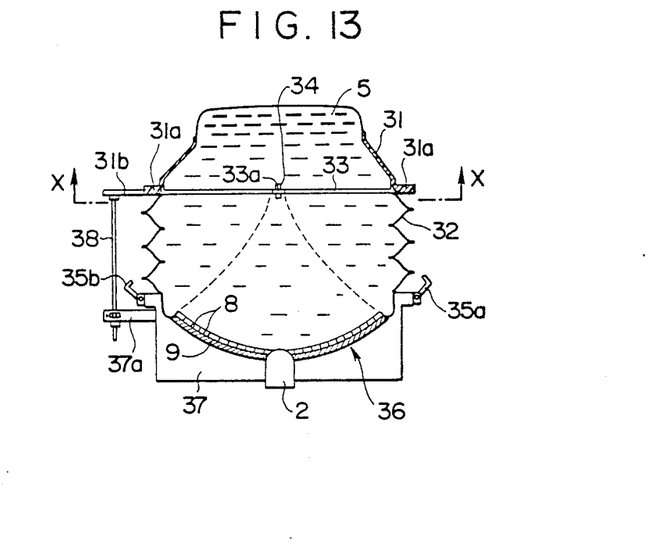
FIG. 13 is a schematic illustration, partly in section, of a ultrasonic therapeutical apparatus according to a third embodiment of the invention, illustrating an operational phase in which the operation of the apparatus is examined.

FIG. 3 shows a third embodiment of the invention which allows the occurrence of any abnormality of a ultrasonic therapeutical apparatus to be examined. The apparatus includes a shock wave generator 36 including a mounting plate 9 of a spherical configuration and which is mounted on a stationary member 37. The ultrasonic observation unit 2 is disposed centrally on the mounting plate 9, and a plurality of ultrasonic vibrators 8 are disposed in a mosaic pattern on the front surface of the mounting plate 9. In the present embodiment, the water bag 5 as mentioned above is disposed immediately in front of the generator 36 and is connected therewith by flexible bellows 32. Specifically, the water bag 5 has its rear edge connected to the bellows 32 in a liquid tight manner through a mounting frame 31 so that the rear surface of the water bag 5 opposes the front surface of the spherical mounting plate 10 on which the ultrasonic vibrators 8 are mounted. The front edge of the bellows 32 is secured to the mounting frame 31 in a liquid tight manner, and the rear edge of the bellows 32 is also connected in a liquid tight manner to the peripheral edge of the mounting plate 9.

Figure 15:
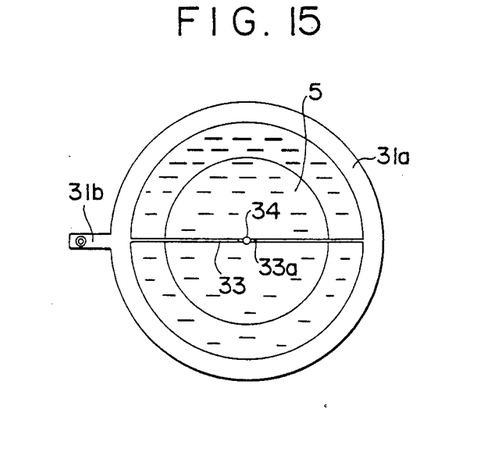
FIG. 15 is a cross section taken along the line X—X shown in FIG. 13.

As shown in FIG. 15, a rod-shaped support member 33 diametrically extends across the mounting frame 31 so as to be located over the center of curvature of the mounting plate 9. In order to avoid interference with the acoustic field of ultrasonic waves generated by the generator 36, the support member 33 comprises a thin rod member and includes a centrally located support 33a on which a ultrasonic sound pressure determining sensor 34 is detachably mounted in the manner illustrated in FIGS. 13 and 15.

At its rear end, the mounting frame 31 which is used to connect the water bag 5 with the shock wave generator 36 through the interposed bellows 32 is peripherally formed with a projecting rib 31a, which is adapted to be engaged with hook members 35a, 35b formed at symmetrical positions on the stationary member 37 when the bellows 32 are folded down to place the water bag 5 directly on the shock wave generator 36, thus positively locking the water bag 5 to the shock wave generator 36.

At a point around the circumference of the projecting edge 31a, there is provided a gauge mounting arm 31b which extends radially outward from the rib 31a, and another gauge mounting arm 37a is also formed on the stationary member 37 in vertical alignment with the gauge mounting arm 31b. A gauge 38 which is used to determine the location of the sensor 34 is detachably connected between the mounting arms 31b, 37a. The location of the sensor 34 which is determined by the gauge 38 is converted into a digital signal, which is fed into CPU which form part of the position signal generating means 4 (see FIG. 19) so as to be used in a manner to be described later.

In operation, before the therapy is conducted, the hook members 35a, 35b are disengaged from the rib 31a to allow the bellows 32 to be extended, thus moving the water bag 5 away from the shock wave generator 36. At the same time, the shock wave generator 36 is activated for operation. It is to be understood that the water bag 5 and the bellows 32 are filled with a ultrasonic wave transmitting liquid such as water. As the water bag 5 moves upward, the sensor 34 moves upward as well. During its movement, the sensor 34 sequentially determines the sound pressure of the ultrasonic wave which is generated by the generator 36, and the movement of the water bag 5 is stopped at a point where the maximum sound pressure is reached. At this time, the focal point of the ultrasonic wave is recognized by means of the gauge 38. The waveform of the ultrasonic wave which is determined by the sensor 34 is monitored by the display unit 3 (see FIG. 19), whereby it can be confirmed whether a predetermined sound pressure and a waveform have been achieved.

In this manner, a focal point of the ultrasonic wave can be accurately determined prior to the initiation of the therapy when using this embodiment, allowing a positioning operation to be achieved in a reliable manner. Also, any abnormality of the apparatus can be detected before the initiation of the therapy, avoiding any serious accident caused to a patient which may otherwise be occasioned by the occurrence of such abnormality. In this manner, a safe therapy is assured.

Figure 14:
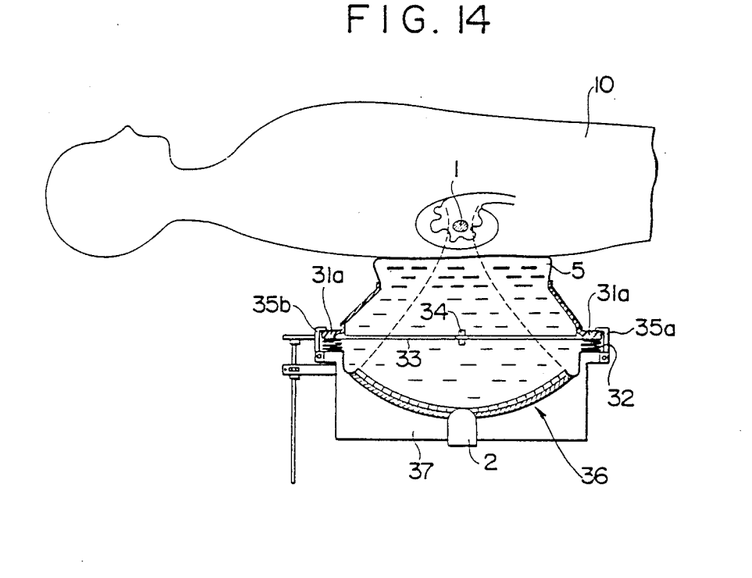
FIG. 14 is a schematic illustration of the apparatus shown in FIG. 13, illustrating the apparatus when it is used to fracture a calculus.

After the confirming operation described above is completed before the initiation of the therapy, the bellows 32 are folded down to its shrunk position as illustrated in FIG. 14, and the hook members 35a, 35b are engaged with the rib 31a to secure the water bag 5 against the generator 36. Thereupon, the combination of the generator 36 and the water bag 5 are configured to be a normal assembly as used in the prior art. Since the sensor 34 is then largely offset from the focal point of the ultrasonic wave, it is not subject to an increased sound pressure, thus avoiding its damage. Because both the support 33a and the sensor 34a are small enough to prevent any concentration of the ultrasonic wave thereon, there occurs no interference with the focussing operation of the ultrasonic wave. Accordingly, the water bag 5 and the generator 36 can be positioned so as to be focussed upon the calculus 1 within the physical body 10 under this condition for fracturing operation.

Thus, the therapeutical apparatus of the present embodiment allows the water bag 5 to be freely displaced with respect to the shock wave generator by means of the bellows 32, with the focal point of the ultrasonic wave located within an extent of movement of the water bag 5 where the sensor 34 is disposed. Accordingly, it is unnecessary to remove the sensor 34 each time the confirming operation is required, thus enabling a greatly facilitated confirmation of the focussing condition of the ultrasonic wave before the initiation of the therapy.

Figure 16:
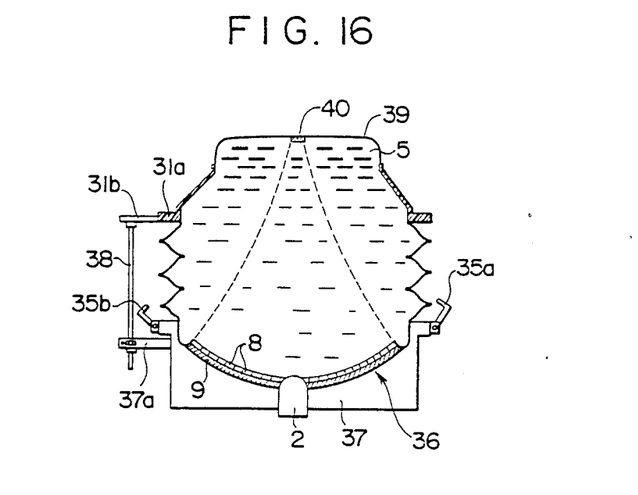
FIG. 16 is a schematic illustration, partly in section, of a ultrasonic therapeutical apparatus according to a fourth embodiment of the invention.

FIG. 16 shows part of a ultrasonic shock wave generator of a ultrasonic therapeutical apparatus according to a fourth embodiment of the invention in detail. In this fourth embodiment, a sensor 40 which is used to determine the sound pressure of the ultrasonic wave is disposed in a different manner, rather then providing the support member 33 as in the third embodiment. Specifically, an area of the water bag 5 which is adapted to contact the surface of a physical body is formed by a freely deformable soft resin diaphragm 39 which permits an efficient transmission of the ultrasonic wave to the surface of the physical body during the therapy. A sound pressure sensor 40 which may be formed of polyvinylidene fluoride is mounted in the back surface of the resin diaphragm 39 at its center, namely, where the focal point of the ultrasonic wave generated by the shock wave generator 36 is defined. In other respects, the arrangement is similar to the third embodiment, and accordingly, corresponding parts are designated by like reference numerals without repeating their description. In this instance, the operation is similar to that of the third embodiment with a similar effect. In addition, the construction is simplified, thus reducing the cost required.

In the third and the fourth embodiment, the sensors 34 and 40 are manually movable, but they may be automatically moved. By way of example, a motor may be mounted on the gage mounting arm 37a to move the rib 31a through transmission means such as a combination of rack and pinion, thus displacing the sensors 34, 40 as well as the gage 37. Because the movement of the sensor is related to its output signal, the motor may be stopped at the position where an output signal from the sensor is at its maximum or where the sensor is located at a focal point, thus allowing the optimum focal point to be detected automatically. In this instance, the resulting position may be checked against a focal point which is previously stored for any displacement.

Figure 17:
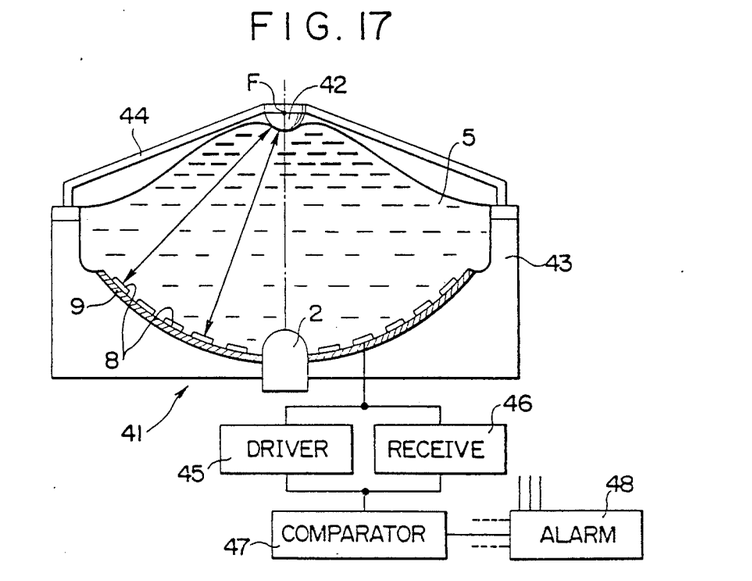
FIG. 17 is a schematic illustration of a ultrasonic shock wave generator of a ultrasonic therapeutical apparatus according to a fifth embodiment of the invention.

FIG. 17 shows a fifth embodiment of the invention which allows any change in the response of individual ultrasonic vibrators used in a ultrasonic shock wave generator to be detected. Specifically, a shock wave generator 41 includes a mounting plate 9, which is in the form of a spherical shell. A plurality of ultrasonic vibrators 8, which may be formed by piezoelectric elements, are mounted on the front surface of the mounting plate 9 so as to be directed toward the focal point F. On the other hand, a ultrasonic reflector 42 in the form of a semi-spherical shell and which may be formed of a material such as stainless steel, for example, which enables an efficient reflection of a ultrasonic wave, is disposed as centered about the focal point F. Specifically, the reflector 42 is detachable mounted on a support member 44 which is carried by a body 43 of the shock wave generator. When the reflector 42 is disposed in this manner, the individual ultrasonic waves generated by the individual vibrators 8 will be returend to the respective vibrators 8 from which they have been transmitted, so as to be received by the corresponding vibrators 8. It is to be noted that the reflector 42 has a semispherical shell configuration, which is centered about the focal point of the ultrasonic wave.

Each ultrasonic vibrator 8 is associated with a respective ultrasonic drive circuit 45 and a reflected wave receiver circuit 46. The circuits 45, 46 are connected to a comparator 47, which is in turn connected to an alarm circuit 48. It is to be understood that the circuits 45, 46 and 47, and a circuit which applies a required voltage to the individual vibrators as well as a circuit which detects a voltage developed upon receiving a reflected ultrasonic wave are conventional. In operation, when it is desired to detect any change which ocurs in the response of the ultrasonic vibrators 8 or piezoelectric elements which form the shock wave generator 41, the reflector 42 is mounted on the support member 44 in the manner illustrated in FIG. 17. Subsequently, the water bag 5 is allowed to expand until its upper end face is brought into close contact with the lower surface of the reflector 42 without leaving any air gap therebetween. Pulse voltages are applied to the individual ultrasonic vibrators 8, through the drive circuit 45, whereby ultrasonic waves are generated and directed toward the focal point F from the respective vibrators 8 and then reflected by the reflector 42 to be returned to the associated vibrators 8, which thus receive the reflection. The applied voltage from the drive circuit 45 may be compared against the received voltage by the comparator 47, thus allowing any degradation in the ultrasonic vibrators 8 or piezoelectric elements, such as a reduced voltage output, to be readily detected. If the piezoelectric elements are degraded to a degree which exceeds a given level, the alarm circuit 48 delivers a warning to a user.

A length of time for the ultrasonic wave generated by the piezoelectric element 8 to be returned by the reflector to such piezoelectric element depends on the course which it travels since the propagation speed of the ultrasonic wave remains constant in this embodiment. If the reflector is located at the focal point, the lengths of time which are required by the individual ultrasonic waves from the respective piezoelectric elements to be returned by reflection from the reflector will all coincide with each other. Accordingly, if any one of the piezoelectric elements produces a different length of time, this indicates the occurrence of a disturbance in the focussing condition. The alarm circuit 48 also provides a warning in this instance. Accordingly, a corrective measure can be taken immediately, thus allowsing the ultrasonic therapeutical apparatus to be used in its optimum condition. For normal operation of the apparatus, the reflector 42 may be removed from the apparatus.

Figure 18:
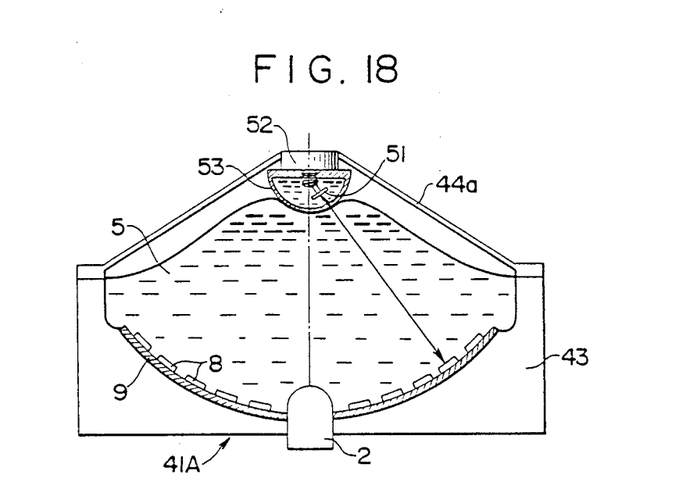
FIG. 18 is a schematic illustration of a ultrasonic shock wave generator of a ultrasonic therapeutical apparatus according to a sixth embodiment of the invention.

FIG. 18 is a schematic view, partly in section, of a shock wave generator of a ultrasonic therapeutical apparatus according to a sixth embodiment of the invention. This apparatus is designed to enable a particular group of piezoelectric elements or a particular piezoelectric element alone to be examined as well as the entire piezoelectric elements.

Specifically, a shock wave generator 41A of this embodiment includes a body 43 on which a support member 44a is detachably mounted. Secured to the support member 44a is a motor 52 which is used to swing a reflecting plate and which is positioned in vertical alignment with the center axis of the mounting plate 9, which is in the form of a spherical shell. An output shaft of the motor 52 has a reflecting plate 51 mounted thereon as by a universal joint for reflecting a ultrasonic wave. It is to be understood that the reflecting plate 51 can be rocked by the motor 52 through an angular extent of substantially 180° including the focal point F of ultrasonic wave so as to be located opposite to each individual ultrasonic vibrator. The reflecting plate 51 is surrounded by a semi-spherical cup 53, the interior of which is filled with a ultrasonic wave transmitting liquid.

When it is desired to detect the response or any degradation thereof of a particular ultrasonic vibrator 8 or a particular group of ultrasonic vibrators which form the shock wave generator 41A, the reflecting plate 51 is suitably rotated by the motor 52 to detect a reflective output therefrom in the similar manner as described above in connection with the third embodiment. The reflecting plate 51 may be sequentially rotated in three dimensions by means of the motor 52, thus allowing the response of all the ultrasonic vibrators 8 to be examined. In this manner, the apparatus of this embodiment is capable of examining the response of any desired piezoelectric element or elements as desired.

What is claimed is:

1. An ultrasonic therapeutic apparatus for treating a target area to be treated within a body by directing and focusing externally generated ultrasonic waves thereto comprising;

an ultrasonic wave generator including a plurality of ultrasonic vibrators for directing and focussing generated ultrasonic waves upon a target area to be treated;

said plurality of ultrasonic vibrators being divided into at least two groups of vibrators, with each of said groups having a different driving frequency;

control means for controlling the phase of the ultrasonic wave generated by each of said groups of ultrasonic vibrators so that ultrasonic waves generated by each of said groups are focussed at the same point at which ultrasonic wave pressure becomes maximum;

said control means also controlling the driving frequencies so that fundamental frequencies of the ultrasonic vibrators of each of said groups have a multiple relation with each other.

2. An ultrasonic therapeutic apparatus according to claim 1 in which for each of said groups the ultrasonic vibrators thereof are arranged in a row and are formed by piezoelectric elements, which are mounted on the front surface of a mounting plate.

3. An ultrasonic therapeutic apparatus according to claim 2 in which the mounting plate is in the form of a spherical shell.

4. An ultrasonic therapeutic apparatus according to claim 2 in which the mounting plate comprises a flat, disc-shaped plate.

5. An ultrasonic therapeutic apparatus according to claim 2 in which the mounting plate has an increasing curvature from its center towards its extremity.

6. An ultrasonic therapeutic apparatus according to claim 2 in which the mounting plate is notched around its peripheral edge.

7. An ultrasonic therapeutic apparatus according to claim 2 in which the mounting plate comprises a flat, square plate which is flexed to define a concave surface.

8. An ultrasonic therapeutic apparatus according to claim 2 in which, for each of said groups the piezoelectric elements thereof are disc-shaped and are disposed in a circular row, said circular rows being concentric.

9. A ultrasonic therapeutic apparatus according to claim 2 in which a plurality of annular piezoelectric elements are disposed on concentric circles.

10. An ultrasonic therapeutical apparatus according to claim 2 in which said piezoelectric elements are disposed in a plurality of aligned vertical and horizontal rows, and each of said piezoelectric elements is disc-or square-shaped.

11. An ultrasonic therapeutic apparatus according to claim 2 in which selected one of said ultrasonic vibrators are formed by Langevin vibrators.

12. An ultrasonic therapeutic apparatus according to claim 2 further comprising means for controlling the output level of the ultrasonic wave by controlling the drive voltage applied to the ultrasonic vibrators.

13. An ultrasonic therapeutic apparatus according to claim 2 further comprising means for controlling the output level of the ultrasonic wave by controlling the number and the variety of ultrasonic vibrators, the thickness of a damping layer applied thereto and a configuration of the ultrasonic vibrators.

14. An ultrasonic therapeutic apparatus according to claim 1 in which the control means includes means for changing the output level of the ultrasonic wave generated by the ultrasonic vibrators.

15. An ultrasonic therapeutic apparatus according to claim 1 in which the control means comprises a plurality of delay circuits each associated with a row of ultrasonic vibrators, and a plurality of shock wave generating circuits connected with the respective delay circuits.

16. An ultrasonic therapeutic apparatus according to claim 15 in which the delay circuits include means for adjusting the phase of the ultrasonic waves generated by the individual ultrasonic vibrators so that these ultrasonic waves are focussed at a single point where an ultrasonic wave from each row has a maximum sound pressure.

17. An ultrasonic therapeutic apparatus according to claim 15 in which the shock wave generating circuit comprises a pulse generator which controls the frequency and the amplitude with which the ultrasonic vibrators in each of said rows are driven.

18. An ultrasonic therapeutic apparatus according to claim 17 in which the frequency with which the particular row of ultrasonic vibrators are driven is chosen to be a multiple of the frequency with which the ultrasonic vibrators of its immediately inner row are driven.

19. An ultrasonic therapeutic apparatus according to claim 18 in which the multiple is equal to two.

20. An ultrasonic therapeutic apparatus according to claim 1 in which for each of said groups the elements thereof are disposed in a row, and the control means controls the distance of each of the rows to the focal point so that the ultrasonic waves from the respective rows are focussed at a single point where they exhibit a maximum sound pressure.

21. An ultrasonic therapeutic apparatus as defined in claim 1 in which said means for controlling the phase comprises delay circuits, each connected with each group of ultrasonic vibrators.

22. An ultrasonic therapeutic apparatus as defined in claim 1 in which said means for controlling the phase controls the distance between each group of the ultrasonic vibrators and the focus point of each group so that the generated ultrasonic waves are focussed at the same point at which the sound pressure of the generated ultrasonic waves of each group of the vibrators becomes maximum.

23. An ultrasonic therapeutic apparatus as defined in claim 1 in which the multiples of the driving frequencies are in a relation of double with each other.

24. An ultrasonic therapeutic apparatus as defined in claim 21 in which said delay circuits control the phase of the ultrasonic waves generated from each ultrasonic vibrator.

25. An ultrasonic therapeutic apparatus as defined in claim 21 in which said control means comprises a plurality of impact wave generating means operatively connected with said delay circuits, and each of said impact wave generating means includes a pulse generator and is adapted to control the frequency and the amplitude of the ultrasonic wave generated from the ultrasonic wave vibrators.

* * * * *

UNITED STATES PATENT AND TRADEMARK OFFICE
CERTIFICATE OF CORRECTION

PATENT NO. : 4,955,366
DATED : Sept. 11, 1990
INVENTOR(S) : Naoki Uchiyama et al.

It is certified that error appears in the above-identified patent and that said Letters Patent is hereby corrected as shown below:

ON TITLE PAGE: Item [75]
        The name of the tenth inventor should read
  --Masaaki Hayashi--.

Signed and Sealed this

Twenty-eighth Day of April, 1992

Attest:

HARRY F. MANBECK, JR.

*Attesting Officer*          *Commissioner of Patents and Trademarks*